United States Patent
Ruben

(10) Patent No.: US 6,787,891 B2
(45) Date of Patent: Sep. 7, 2004

(54) FREEFORM SUBSTRATES AND DEVICES

(75) Inventor: David A. Ruben, Mesa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 201 days.

(21) Appl. No.: 09/731,121

(22) Filed: Dec. 6, 2000

(65) Prior Publication Data

US 2002/0066940 A1 Jun. 6, 2002

(51) Int. Cl.[7] .............................................. H01L 23/06
(52) U.S. Cl. ...................... 257/684; 257/723; 257/724
(58) Field of Search .............................. 257/684, 723, 257/724, 678, 686; 607/36

(56) References Cited

U.S. PATENT DOCUMENTS

| | | | | |
|---|---|---|---|---|
| 4,692,147 A | * | 9/1987 | Duggan | 604/891.1 |
| 4,783,225 A | | 11/1988 | Maejima et al. | 148/33.2 |
| 5,230,747 A | | 7/1993 | Maejima et al. | 148/33.2 |
| 5,279,992 A | | 1/1994 | Maejima et al. | 437/229 |
| 5,370,669 A | * | 12/1994 | Daglow et al. | 607/36 |
| 5,431,695 A | * | 7/1995 | Wiklund et al. | 607/36 |
| 5,439,482 A | * | 8/1995 | Adams et al. | 607/5 |
| 5,456,698 A | * | 10/1995 | Byland et al. | 607/36 |
| 5,470,345 A | * | 11/1995 | Hassler et al. | 607/36 |
| 5,697,953 A | * | 12/1997 | Kroll et al. | 607/5 |
| 5,749,910 A | * | 5/1998 | Brumwell et al. | 607/36 |
| 5,782,891 A | * | 7/1998 | Hassler et al. | 607/36 |
| 5,873,899 A | * | 2/1999 | Stutz et al. | 607/36 |
| 6,014,586 A | * | 1/2000 | Weinberg et al. | 607/36 |
| 6,094,597 A | * | 7/2000 | Wold | 607/5 |
| 6,191,931 B1 | * | 2/2001 | Paspa et al. | 361/302 |
| 6,192,277 B1 | * | 2/2001 | Lim et al. | 607/37 |
| 6,256,206 B1 | * | 7/2001 | Van Campenhout | 361/760 |
| 6,459,566 B1 | * | 10/2002 | Casby et al. | 361/517 |

FOREIGN PATENT DOCUMENTS

| | | | | |
|---|---|---|---|---|
| JP | 7161875 | 6/1995 | | H01L/23/28 |
| JP | 7307316 | 11/1995 | | H01L/21/304 |

* cited by examiner

Primary Examiner—Jerome Jackson
Assistant Examiner—Eugene Lee
(74) Attorney, Agent, or Firm—Girma Wolde-Michael; Daniel G. Chapik

(57) ABSTRACT

An implantable medical device substrate is free form cut to the shape of the interior of the device. The free form shape allows more efficient use of not only the interior space of the device but also of the substrate itself. Integrated circuit components are formed to fit the shape of the substrate, freeing areas in the device for additional components, or allowing the device to be made smaller through a maximized use of the available space-volume.

6 Claims, 4 Drawing Sheets

FREEFORM SUBSTRATES AND DEVICES

The present invention relates generally to semiconductor substrates, and more specifically to non-straight edged substrates for use in medical devices.

BACKGROUND

Traditionally, integrated circuit substrates and integrated circuit dice are cut or scribed from larger pieces of material in known shapes. Cutting and scribing implements for such dice and substrates are only capable of cutting or scribing along a straight line. The resulting substrates and dice formed by traditional cutting and scribing are, therefore, comprised of all straight line edges. Traditional shapes for such dice and substrates are rectangles and parallelograms, although other polygonal shapes such as octagons and the like have been used. However, all the resultant dice and substrates typically comprise of straight edges.

Such straight edges are preferred for use in semiconductor fabrication, because arrangement of the integrated circuits and the like is made easier by having similar shapes. However, in certain areas, such as the field of implantable medical devices, substrates and even integrated circuits are held to extremely tight size specifications. Since the overall trend in implantable medical devices is toward smaller and smaller sizes, and since rough edges and sharp corners are preferably avoided in many implantable medical devices (IMDs), substrates in IMDs often have wasted space and volume due to rounded edges, and have real estate on the die that is unavailable for use due to the restraints on integrated circuit shapes.

Silicon devices and substrates have traditionally been scribed and broken along cleavage planes, or diced in straight lines with a diamond impregnated cutting blade. As such, the edges of the resultant dice and devices are generally straight. For packing efficiency, it is desirable to use an electronic module or substrate that exactly or very closely matches the shape of the product to be developed or used. However, many electronic devices, especially in the implantable medical device field, are not cubic or box-shaped. Instead, they can take on many different shapes, often with curved edges and contours. From an IMD device standpoint, cubes and boxes are not a good match. From a design perspective, however, straight edge devices are not desirable. Further, since curved edges are prominent in IMDs, rectangular silicon devices and substrates are inefficient from a packaging density standpoint.

Silicon has a number of benefits as a substrate material, in that it is readily available, and also processes and methods for preparing and working with Silicon are known in the art.

SUMMARY OF THE INVENTION

In one embodiment, a substrate for an implantable medical device includes a substrate body formed to conform to the shape of the implantable medical device, and a number of integrated circuits formed on the body. The integrated circuits are in another embodiment formed to fit the contoured edges of the substrate.

In another embodiment, an implantable medical device includes a body and a substrate positioned in the body, the substrate having medical device circuitry formed thereon. The substrate has edge contours formed to fit the interior dimension of the substrate body.

In still another embodiment, method for improving package density in an implantable medical device includes creating a free formed substrate shaped with curved edge contours to conform to interior edges of a body of the implantable medical device, and forming integrated circuits on the free formed substrate to use previously unused portions of the substrate.

DETAILED DESCRIPTION

In the following detailed description of the embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention.

Figure 1:
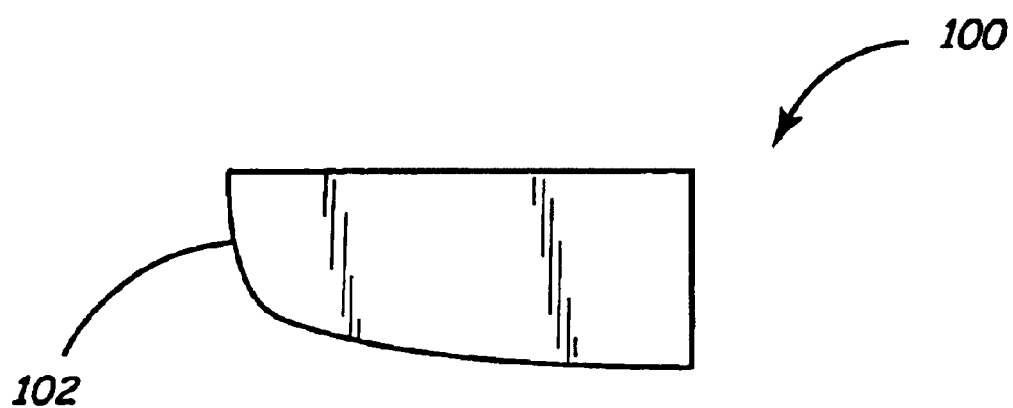
FIG. 1 is a view of a freeform cut substrate according to an embodiment of the present invention.

FIG. 1 is a block diagram view of an embodiment 100 of a substrate of non-traditional shape formed by freeform cutting of the substrate. Substrate 100 has non-straight line edge 102. In one embodiment, the substrate 100 is formed from Silicon. In this embodiment, one of a number of freeform cutting methods is employed to cut the silicon to a desired shape. In one embodiment, the desired shape conforms with that of the inner contours of an implantable medical device, such as a pacemaker, defibrillator, or the like. Such devices are traditionally not box-shaped, but instead have curved edges and contours that allow their implantation or disposition into the human body with less difficulty than an IMD with sharp edges or the like.

Figure 2:
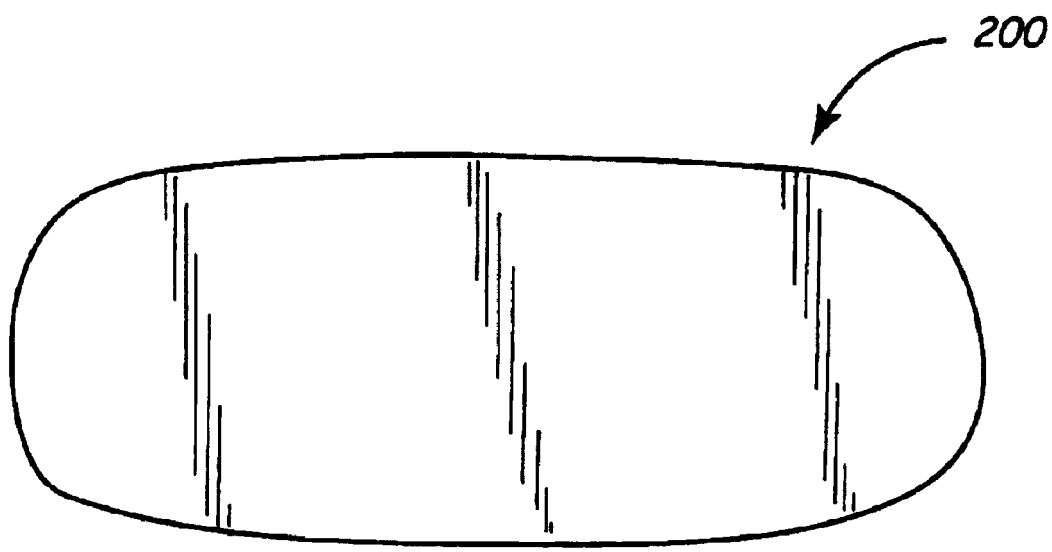
FIG. 2 is a view of another freeform cut substrate according to an embodiment of the present invention.

Another embodiment of a substrate 200 is shown in FIG. 2. Substrate 200 has another shape that has been cut to fit the inner contours of an implantable medical device. It should be understood that the freeform shape of a substrate will depend upon the shape of the body of the device in which it is placed. With the availability of freeform cutting devices and methods, the substrate of each individual device is capable of being cut exactly to conform to the contours of the device. The conformal shape of the device and the substrate increases the available real estate for components and integrated circuits in the device.

Figure 3A:
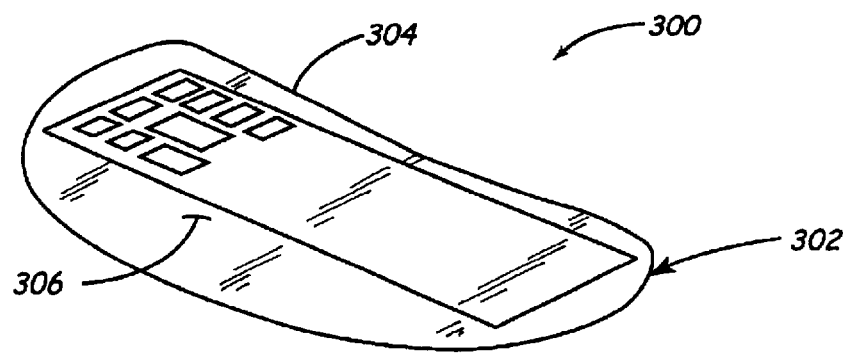
FIG. 3A is a perspective view of a body and substrate of a typical implantable medical device.
Figure 3B:
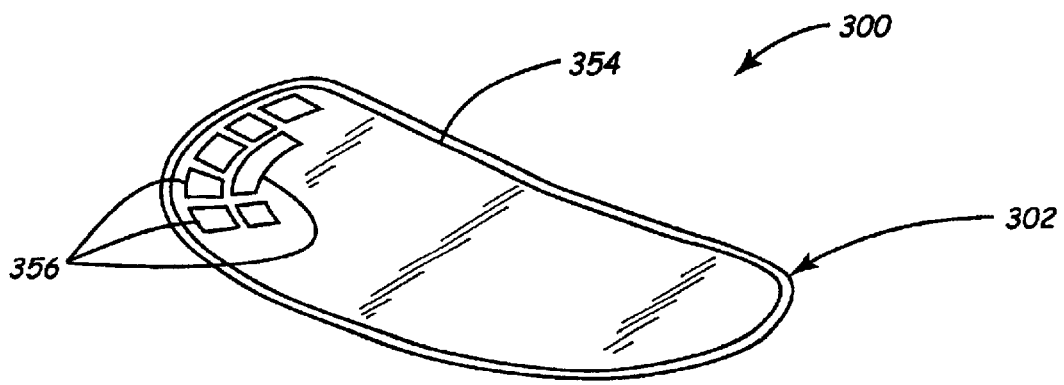
FIG. 3B is a perspective view of a body of an implantable medical device and a substrate according to another embodiment of the present invention.

Further, the availability of freeform cut substrates and improved use of real estate allows in various embodiments the overall device size to be reduced. This is due to the fact that with a substrate that has curved edge contours, more substrate per area is available. FIGS. 3A and 3B show a typical body 302 of an implantable medical device 300 having a traditional substrate 304 (FIG. 3A) and a freeform substrate 354 (FIG. 3B). Substrate 304 is scribed or cut along its straight line edges. Space 306 around the edges of the substrate 304 is unavailable for placement of components on the substrate 304. The restricted shape of the substrate 304 wastes space 306 in the body 302 of implantable medical device 300.

FIG. 3B shows the same body 302 of an implantable medical device 300 with a freeform cut substrate 354. Substrate 354 is not limited to traditional scribed or straight edged substrate shapes. Instead, substrate 354 closely follows the contour of the body 302. The wasted space 306 of FIG. 3A is greatly reduced. The available substrate real estate for the body 302 is increased by the freeform substrate 354 without increasing the size of the body 302.

Figure 3C:
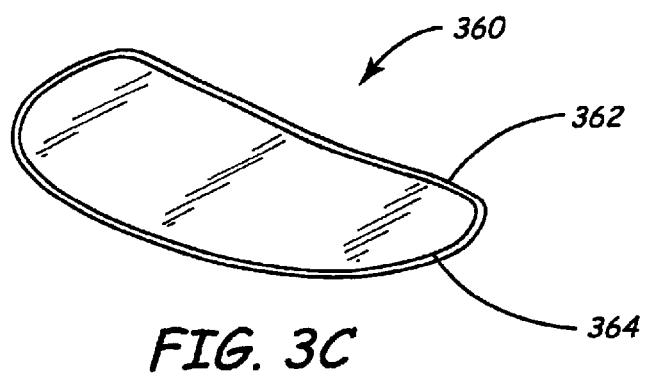
FIG. 3C is a perspective view of a body of an implantable medical device and a substrate according to another embodiment of the present invention.

FIG. 3C shows a smaller implantable medical device 360 having body 362 and freeform substrate 364. Once again, as in FIG. 3B, wasted space between the body 362 wall and the substrate 364 edge is greatly reduced. In this embodiment, the available real estate of an IMD is maintained the same, but the body size is reduced.

Figure 4:
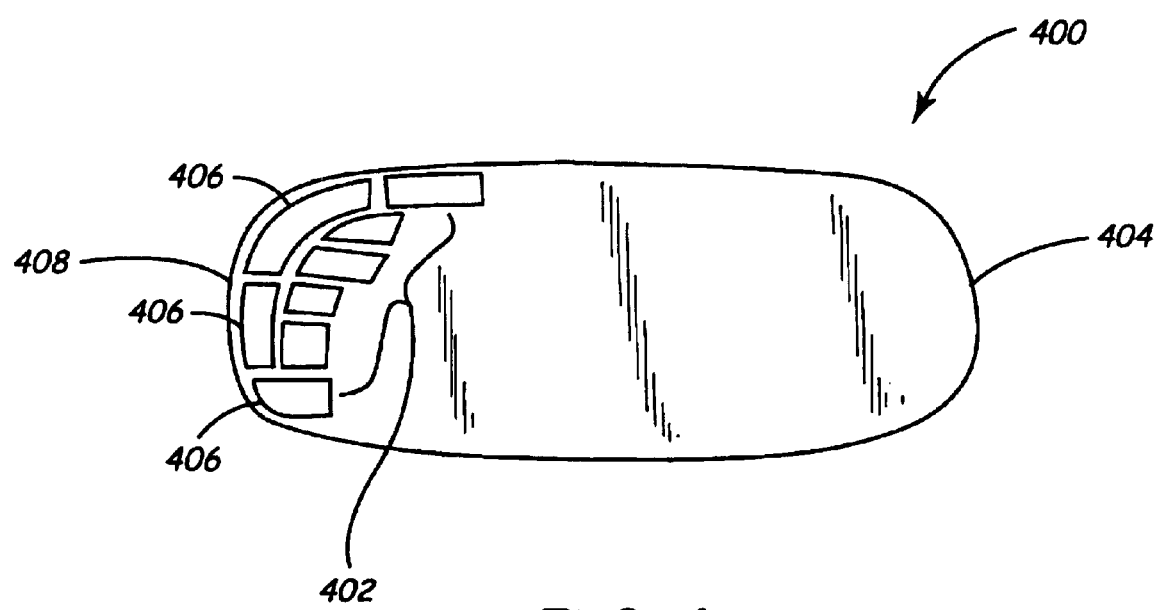
FIG. 4 is a top view of a freeform substrate and integrated circuit components according to another embodiment of the present invention.

In another embodiment 400 shown in FIG. 4, actual devices 402 are formed on the IMD body shaped substrate 404. The devices 402 are formed with patterns and contours to fit the substrate 404. The conformity to the substrate edges increases packing density by using previously unused portions of both the substrate and the body interior for components. This increases available interior space in an IMD for other components. Such other components are used in various embodiments to provide increased functionality, better battery life, better shielding, and the like. With increased usage of the real estate of substrate 404, that is, that more components are formed on the substrate, additional real estate is freed for other components and the like.

In this embodiment, silicon integrated circuit devices 402 have edge contours 406 that match the edges 408 of the substrate 404. The formation of these integrated circuits 402 to the shape of the edge 408 of the substrate 404 eliminates the waste of otherwise unusable or poorly used areas between the straight edges of typical dice and the curved edges of the substrate. By forming such devices 402 in conformal patterns, an increased number of devices such as devices 402 fit into the existing real estate area.

The improvements to available real estate by freeform cutting the substrate are numerous, and include by way of example one or more of the following: reduced waste of space, reduced size and volume, increased availability of space for extra components, and the like.

Additionally, the use of silicon for the substrate material allows the formation of components directly on the substrate. Silicon is especially useful for substrates because it allows such formation of embedded components like transistors, integrated circuits, and high power components, for example. Such components are integrated into the substrate in various embodiments. In the formation of such components directly on or embedded in the substrate, contoured components are also available. This further increases the availability of real estate by allowing not only less wasted space in the body of an implantable medical device, but also less wasted space on the substrate itself. Such contoured components 356 are shown also in FIG. 3B.

Freeform cutting is highly beneficial in areas where real estate is oddly shaped and normal substrates and ICs even do not fill the real estate well, wasting space. A freeform cut substrate can conform to the shape of an IMD so that little real estate at least for the substrate is wasted. Further, since the ICs themselves can be formed on substrates having freeform shapes, those shapes can conform also to the contours and shapes of the IMDs, therefore utilizing valuable real estate instead of wasting it.

Figure 5:
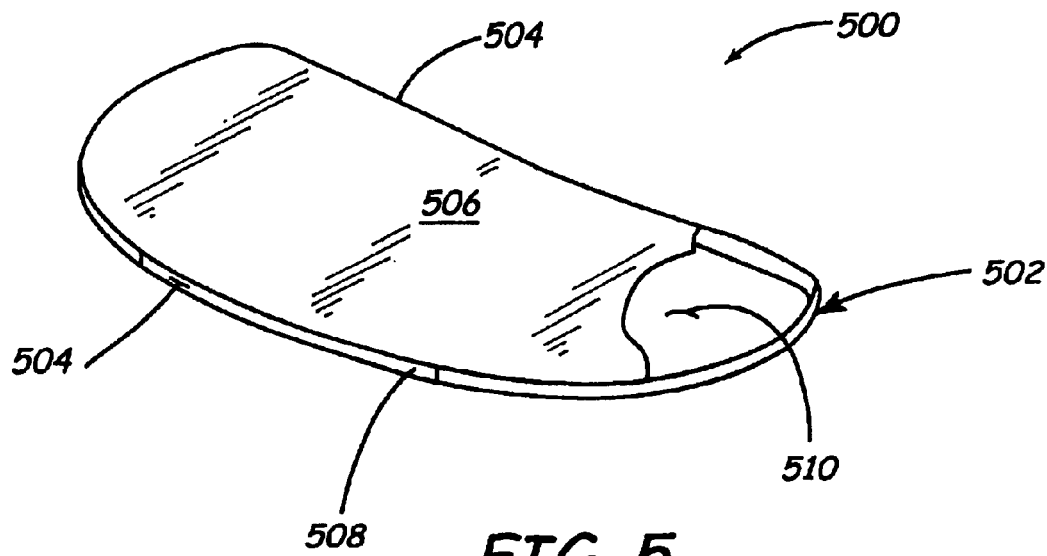
FIG. 5 is a perspective view of an implantable medical device according to another embodiment of the present invention.

FIG. 5 shows an embodiment of an implantable medical device 500. The type of implantable medical device will vary depending upon its function, as will the shape of the IMD 500, without departing from the scope of the invention. IMD 500 has a body 502 having edges 504 and a top 506 and bottom 508. The interior chamber 510 of the implantable medical device 500 is the location for the internal components of the IMD 500. Such components may include but are not limited to telemetry devices, pacing circuitry, control circuitry, batteries, and the like. The circuits within the IMD are typically integrated circuits formed on a substrate such as substrates 100 and 200 discussed above.

A freeform substrate such as the substrates discussed above is cut into the free form shape in any number of ways. Cutting methods for freeform cutting of substrates include using a water laser cutting system such as that developed by Synova, S. A. of Switzerland. The Synova laser cutting system uses a concentrated stream of water as a waveguide for a laser. The laser ablates material from the substrate, and the water stream acts to cool the substrate and to wash away debris created by the ablation.

In various other embodiments of the present invention, the silicon substrate is cut using one of a variety of freeform cutting tools, including but not limited to water laser, $CO_2$ laser, high frequency short wavelength short pulse lasers, and the like.

Figure 6:
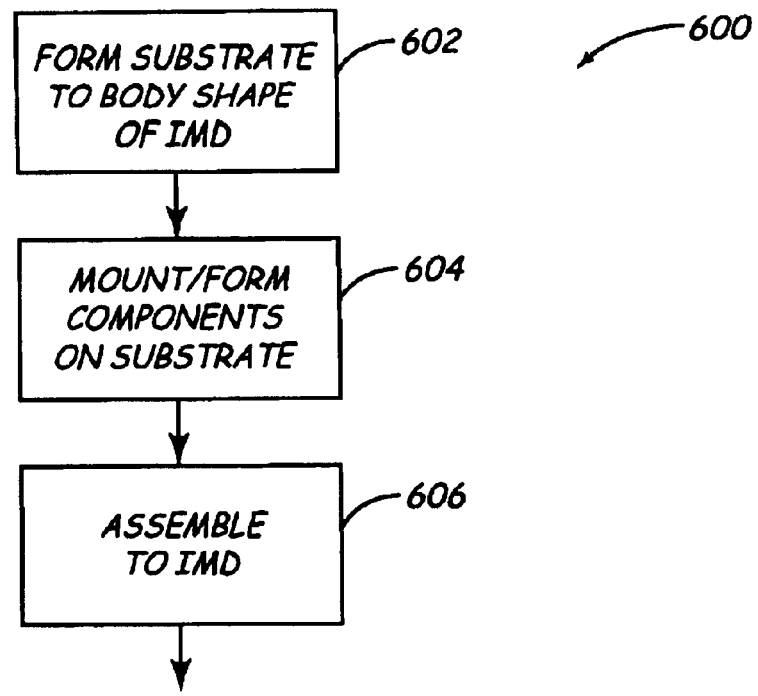
FIG. 6 is a flow chart diagram of a method according to another embodiment of the present invention.

FIG. 6 is a flow chart diagram of a method 600 for increasing packaging density in an implantable medical device. Method 600 comprises in one embodiment forming a silicon substrate to fit the shape of a body of an implantable medical device in block 602, and mounting components to the silicon substrate or forming components on or embedded in the substrate in block 604. In block 606, the silicon substrate is assembled into an implantable medical device body with other necessary components of the IMD.

The method 600 is suitable for use in any device which has a need for increased packaging density, and is very well suited for use in implantable medical devices. In one embodiment, the components of the implantable medical device are formed such that they fit the contours of the formed substrate. In another embodiment, the components are actually formed on the substrate, and are formed to align with the edges of the substrate so as to increase efficient use of the substrate.

The cutting of silicon to any desired shape increases design options and packaging density not only for substrates, but also for integrated circuits and devices containing the substrates and integrated circuits. For example, substrates shaped to be used in implantable medical devices along with integrated circuits that are used with the formed substrates allow the use of a larger portion of available real estate in the IMD, reducing the wasted space and allowing more components to be used in the same amount of space.

In another embodiment, silicon is shaped in a freeform cutting method such as those described above to form smart leads for a device. In still another embodiment, freeform cutting techniques are used for drilling holes in silicon to make vias to connect both sides of the device. Further uses include cutting openings to allow a component to pass through or be bonded on both sides of a substrate.

In various embodiments, substrates for an implantable medical device are cut to fit the contours of the body of the device. The use of such freeform cut substrates improves use of real estate within the limited space constraints of a typical implantable medical device. The ability to cut a substrate such as a silicon substrate to the interior shape of an implantable medical device allows the space to be used more efficiently. When a silicon substrate is used, devices such as transistors, capacitors, integrated circuits, and high power components can be formed using the substrate and embedded therein. Such components are contoured at their edges to conform to the shape of the substrate, further increasing efficient usage of not only the available interior space of the implantable medical device, but also use of substrate real estate.

It is to be understood that the above description is intended to be illustrative, and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable medical device, comprising:
    a body with an exterior configuration with curved edges and contours and defining an internal chamber for circuitry implementing a therapy delivery function;
    a silicon substrate disposed within the internal chamber of the device body, said substrate having silicon integrated circuit device components implementing the therapy delivery function formed directly thereon, and wherein the substrate is formed to fit the curved edges and contours of the body configuration.

2. The IMD of claim 1, wherein the components conform to an edge of the substrate.

3. The IMD of claim 1, wherein the body includes a curved surface, and the substrate is curved to fit the curved surface.

4. The IMD of claim 1, wherein the components are embedded in the substrate.

5. The implantable medical device a claim 1, wherein the substrate includes edge contours formed to fit an interior dimension of the interior chamber of the device body.

6. The implantable medical device of claim 5, wherein the substrate is cut to shape conforming to the internal chamber of the device body using a freeform cutting method.

* * * * *

UNITED STATES PATENT AND TRADEMARK OFFICE
CERTIFICATE OF CORRECTION

PATENT NO.    : 6,787,891 B2
DATED         : September 7, 2004
INVENTOR(S)   : David A. Ruben It is certified that error appears in the above-identified patent and that said Letters Patent is hereby corrected as shown below:

<u>Column 6,</u>
Line 15, delete "cut to shape" and insert -- cut to a shape --.

Signed and Sealed this

Twenty-fourth Day of May, 2005

JON W. DUDAS
*Director of the United States Patent and Trademark Office*